United States Patent [19]

Gupton et al.

[11] Patent Number: 4,612,389

[45] Date of Patent: Sep. 16, 1986

[54] TREATMENT OF WASTE STREAM FROM PENTAERYTHRITOL MANUFACTURE

[75] Inventors: Frank Gupton, Virginia Beach, Va.; Harry E. Ulmer, Morristown, N.J.

[73] Assignee: Virginia Chemicals Inc., Portsmouth, Va.

[21] Appl. No.: 376,933

[22] Filed: May 10, 1982

Related U.S. Application Data

[63] Continuation-in-part of Ser. No. 322,555, Nov. 18, 1981, abandoned.

[51] Int. Cl.$^4$ .................. C07C 29/78; C07C 29/86; C07C 31/24; C07C 51/43; C07C 51/47; C07C 51/48; C07C 53/06
[52] U.S. Cl. .................. 562/513; 562/609; 568/853; 568/854
[58] Field of Search ............. 562/513, 609; 568/854, 568/853

[56] References Cited

U.S. PATENT DOCUMENTS 3,875,248 4/1975 Prinz .................. 568/854
4,083,931 4/1978 Lee .................. 562/609

*Primary Examiner*—Vivian Garner
*Attorney, Agent, or Firm*—DePaoli & O'Brien

[57] ABSTRACT

This invention provides a process for improving the separation and recovery of metal formate and pentaerythritol as crystalline products, from an aqueous waste stream of a pentaerythritol manufacturing operation which involves the reaction of formaldehyde with acetaldehyde in the presence of a metal hydroxide catalyst.

The pentaerythritol process waste stream is passed through a macroreticular resin bed to remove organic byproducts, and the purified waste stream is then evaporatively concentrated to produce crystalline sodium formate product. The resultant mother liquor is diluted with water-miscible alkanol to precipitate a pentaerythritol-metal formate mixture. The precipitate is washed with a portion of waste stream feed to dissolve the metal formate and yield undissolved crystalline pentaerythritol as a product.

At least about 85 percent of the metal formate and at least about 90 percent of the pentaerythritol contained in the original waste stream are recovered as products of the process.

6 Claims, 2 Drawing Figures

TREATMENT OF WASTE STREAM FROM PENTAERYTHRITOL MANUFACTURE

This patent application is a continuation-in-part of patent application Ser. No. 322,555, filed Nov. 18, 1981, now abandoned.

BACKGROUND OF THE INVENTION

In an important industrial process for producing pentaerythritol (PE), formaldehyde is reacted with acetaldehyde in the presence of metal hydroxide catalyst, and the main bulk of the pentaerythritol product is recovered from the aqueous reaction medium by crystallization. Typical pentaerythritol processes are described in U.S. Pat. Nos. 2,790,836 and 3,968,176.

The aqueous mother liquor resulting from the manufacture of pentaerythritol is a waste byproduct stream containing metal formate, unrecovered pentaerythritol, and soluble organic byproduct materials formed in the pentaerythritol synthesizing reaction, including lesser quantities of dipentaerythritol and tripentaerythritol, small quantities of pentaerythritol formals, and formose sugars which tend tocause some difficulty during crystallization of the pentaerythritol and continue to interfere with treatment of the aqueous waste stream.

This aqueous waste stream represents a difficult waste disposa problem, even though it contains metal formate (e.g., sodium formate) of substantial commercial value. If it is attempted to recover the metal formate by conventional evaporative crystallization procedures, these organic materials become concentrated in the crystallization mother liquor and cause it to become quite viscous, thereby hampering crystal separation from the liquor and contaminating the separated crystals. In practice, the recovery of useful metal formate from the liquor is limited to only about 75% of the total metal formate present, owing to these factors. Consequently, a substantial quantity of viscous organic-rich material is produced as a byproduct, which still poses a formidable waste disposal problem.

The potential for recovery of valuable byproducts contained in the aqueous waste stream of a pentaerythritol manufacturing operation has invited various developments which have been reported in the prior art literature.

U.S. Pat. No. 2,441,602 describes an aqueous waste stream treatment method which involves concentrating the stream by water removal, diluting the concentrated stream with a water-soluble monohydric alcohol and heating the diluted mixture, then separating the undissolved metal formate by filtration, distilling the filtrate solution to remove most of the water as an azeotrope with the alcohol, and subsequently cooling the solution to produce crystallized metal formate and pentaerythritol.

U.S. Pat. No. 2,617,791 describes a process for treating pentaerythritol mother liquor which involves heating the mother liquor with a fatty acid at 175°-275° C. until an oily phase and a solids phase are formed, and thereafter recovering the oily layer which contains fatty acid esters of the polyhydroxy compounds.

U.S. Pat. No. 2,780,655 describes a method of treating pentaerythritol mother liquor which involves concentrating the mother liquor to form a slurry of solid pentaerythritol and metal salts, adding formalin to the slurry to dissolve the pentaerythritol, and recovering the undissolved salts.

U.S. Pat. No. 3,179,704 describes a method of treating pentaerythritol mother liquor which involves evaporating the mother liquor to dryness, admixing the resulting dried solids with dimethylformamide to dissolve the organic materials, and separating the extract solution from the undissolved formate salts.

U.S. Pat. No. 3,766,277 describes a process which involves (1) contacting a pentaerythritol waste stream with tertiary-butanol to extract pentaerythritol; (2) optionally, purifying the extract phase with charcoal or macroreticular resin; and (3) recovering pentaerythritol from the purified extract phase by crystallization.

U.S. Pat. No. 3,875,248 describes a pentaerythritol recovery process which involves (1) passing pentaerythritol reaction product mixture through a macroreticular resin to remove organic materials, excepting pentaerythritol; and (2) subjecting the purified stream to concentrating and cooling procedures to precipitate crystalline pentaerythritol. The pentaerythritol product mixture is obtained directly from the formaldehyde/acetaldehyde reaction step and contains all of the pentaerythritol product. Preferably, the reaction product mixture is concentrated prior to the purification treatment with macroreticular resins in step(1).

Other United States Patents of general interest relating to the production and recovery of pentaerythritol and various byproducts include U.S. Pat. Nos. 2,004,010; 2,223,421; 2,270,839; 2,386,289; 2,696,507; 2,719,867; 2,782,918; 2,790,011; 2,790,836; 2,790,837; 2,820,066; 3,379,624; 3,478,115; 3,875,248; 3,968,176; 4,083,931; and references cited therein.

Because of environmental and economic considerations, as indicated by the prior art references disclosed hereinbefore, there have been continuing investigative efforts to develop methods for recovering the valuable organic and inorganic components of waste byproduct streams such as that associated with pentaerythritol production. However, the recovery processes that have been proposed for the pentaerythritol mother liquor have been hampered by difficulties with undesirably high viscosities, contamination by unwanted components, formation of new byproducts requiring additional treatment, and the like. Among such prior art recovery processes, for example, it is known to recover sodium formate from a pentaerythritol waste stream by evaporative crystallization and then to incinerate the aqueous mother liquor (containing, for example, 36–44% sodium formate, 14–18% pentaerythritol, and 18–22% of other organic impurities, in addition to water). However, the amount of inorganic material, in the form of suspended solids, in the waste stream being incinerated affects flame stability. Combustion of sodium formate causes a buildup of sodium carbonate that creates operational problems. Excessive amounts of water in the feed, in addition to other factors, results in low heat recovery which is economically undesirable.

There remains a need for a new and improved procedure for treatment of waste byproduct streams derived from large scale chemical manufacture.

Accordingly, it is a main object of the present invention to provide an improved process for recovering organic and inorganic values from the aqueous waste stream derived from pentaerythritol manutacture.

It is another ooject of this invention to provide a process for recovering as separate products of high purity substantially all of the metal formate and pentaerythritol contained in an aqueous waste stream derived from pentaerythritol production, in which production formaldehyde is reacted with acetaldehyde in the presence of a metal hydroxide catalyst.

It is a further object of this invention to isolate a residual organic byproduct concentrate of high fuel value from an aqueous waste stream derived from pentaerythritol production.

Other objects and advantages of the present invention shall become apparent from the accompanying description and examples.

DESCRIPTION OF THE INVENTION

One or more objects of the present invention are accomplished by the provision of a process for recovering inorganic and organic values from an aqueous waste stream derived from pentaerythritol production in which formaldehyde is reacted with acetaldehyde in the presence of a metal hydroxide catalyst, wherein said aqueous stream contains metal formate, pentaerythritol and organic byproducts, said process comprising (1) passing the aqueous waste stream through a macroreticular acrylic ester resin bed to remove organic byproducts and provide a purified aqueous waste stream; (2) evaporatively crystallizing the purified aqueous waste stream to form crystalline metal formate and a concentrated aqueous mother liquor; (3) separating and recovering the crystalline metal formate as a product from the concentrated aqueous mother liquor, and diluting the said mother liquor with water-miscible alkanol to form a precipitated pentaerythritol-metal formate crystalline mixture and an aqueous alkanolic mother liquor; (4) separating the pentaerythritol-metal formate crystalline mixture from the aqueous alkanolic mother liquor; and (5) contacting said crystalline mixture with a portion of the original aqueous waste stream to dissolve selectively the crystalline metal formate and form a metal formate-enriched aqueous waste stream, and yield undissolved crystalline pentaerythritol as a product.

A typical aqueous pentaerythritol process waste stream nominally has a content which corresponds to the following composition:

| | |
|---|---|
| Metal formate | 28.3% |
| Metal sulfate | 0.3% |
| Pentaerythritol | 5.4% |
| Other organics | 7.5% |
| Water | 58.5% |

The total organic content of the waste stream usually will average in the range of about 10–20 weight percent.

The metal hydroxide catalyst involved in the pentaerythritol manufacture is usually an alkali metal hydroxide, and is preferably either sodium hydroxide or potassium hydroxide. Correspondingly, the metal formate component being recovered by the present invention process is an alkali metal formate particularly sodium formate.

An important aspect of the present invention process is the step(1) passage of the aqueous waste stream through a specific type of resin bed, i.e., a macroreticular acrylic ester resin bed. For purposes of the present invention, optimal results are obtained if the resin selected for the bed is a macroreticular acrylic ester resin such as Amberlite XAD-7 (Rohm and Haas Company).

Macroreticular resins are synthetic water-insoluble non-ionic hydrated porous polymers in bead form which are further characterized by having a unique macroreticular physical porosity, high surface area, and substantially uniform pore size distribution. They have good thermal stability and can be employed at temperatures of 150° C. and higher. An Amberlite XAD-7 type of polymeric adsorbent is a crosslinked acrylic ester polymer which is supplied commercially in the form of 20–60 mesh beads. This type of resin has excellent physical durability and can be used in columns with repeated exhaustion and regeneration cycles in both upflow and downflow operation.

In adsorption of organic molecules from aqueous or other polar solvents, the hydrophilic and hydrophobic portions of the solute are both adsorbed onto the resin surfaces. Polar bonding (for example, hydrogen bonding) occurs between the hydrophilic portion of the sorbate molecule and the aliphatic surface of the said Amberlite XAD-7 type of resin, in addition to the normal van der Waals' interactions between the hydrophobic portion and the adsorbent.

The dissolution of organic molecules in water is accompanied by a negative entropy change, resulting from orientation of water molecules around the organic species. As organic molecules are adsorbed onto the surface of the adsorbent, the oriented water molecules are released, with accompanying entropy increase. This entropy gain is the principal driving force in physical adsorption of organic molecules from aqueous systems such as are described in the present invention.

The macroreticular acrylic ester resin employed as a step(1) adsorbent substrate can be further characterized as having one or more of the following properties:

| | |
|---|---|
| Solids, % | 28–33 |
| Porosity, ml pores/ml bead | 0.5–0.55 |
| Surface area, sq. m/gm dry basis | 440–460 |
| Average pore diameter, Å | 75–85 |
| True wet density, gm/ml | 1.0–1.1 |
| Skeletal density, gm/ml | 1.2–1.3 |
| Bulk density, gm/cc | 0.6–0.7 |

The choice of particular adsorbent bed in step(1) is significant, since it has been found that various macroreticular resins are either unsuitable or less versatile than the specific Amberlite XAD-7 type of acrylic ester resin employed in step(1) of the present invention process.

Thus, Amberlite XAD-1 and Amberlite XAD-2 are disclosed in U.S. Pat. No. 3,875,248 as being suitable for adsorbing pentaerythritol formals and formose sugars and other organic byproducts contained in a pentaerythritol manufacture type of aqueous waste steam. However, these waste streams differ in the nature and quantity of the organic byproduct content, depending on the particular plant procedure being employed in pentaerythritol production.

For example, in some procedures the aqueous reaction medium which is the precursor to the subsequent aqueous waste stream is subjected to heating under acidic conditions (e.g., in the presence of sulfuric acid or formic acid). One result of the acidic treatment is the hydrolytic conversion of organic byproducts such as pentaerythritol formals.

For the step(1) treatment of a pentaerythritol process waste stream which contains hydrolyzed organic byproducts, it has been found that an Amberlite XAD-7 type of resin is a highly efficient adsorbent for the hydrolyzed organic byproducts, while other macroreticular resins are ineffective for such purpose. This is illustrated by the following comparative data (employing Rohm and Haas resins) with respect to a pentaerythritol process waste stream containing acid-hydrolyzed organic byproducts:

| Resin | % Removal of Organic Impurities |
| --- | --- |
| Amberlite XAD-1 | 18.7 |
| Amberlite XAD-2 | 23.2 |
| Amberlite XAD-4 | 22.7 |
| Amberlite XAD-7 | 69.5 |

The Amberlite XAD-7 type of macroreticular acrylic ester resin employed in the step(1) adsorbent bed procedure of the present invention is versatile in that it can adsorb efficiently the organic byproduct content of a pentaerythritol process waste stream, whether or not the organic byproducts have been converted under acid hydrolysis conditions.

As described more fully hereinafter with respect to Example II and FIG. 1, the macroreticular resin bed employed in step(1) is periodically regenerated by washing with an eluant. In general, the eluant must be a good solvent for the sorbate, since elution is based upon preferential migration of the sorbate into the solvent phase. If a non-polar solvent is used as eluant, it will be necessary to displace this with a co-solvent, such as alkanol, before the resin bed can be rehydrated and placed in a succeeding adsorption cycle.

If a polar water-miscible eluant is used, the alkanol soak can be eliminated, but a downflow rinse with water is desirable to remove all the eluant prior to the next adsorption cycle.

Illustrative of suitable eluants are water-miscible $C_{1-3}$-alkanols such as methanol, ethanol, ethylene glycol, methoxyethanol, propanol and isopropanol.

The wash effluent from the resin bed regeneration procedure usually will be subjected to distillation to yield eluant for recycle and a residual organic byproduct stream. This said organic byproduct stream has excellent burning properties and can be combusted for its fuel value, which end use has the advantage of simultaneously functioning as a convenient waste disposal means.

With further reference to the invention process, the water-miscible alkanol employed in step(3) as a pentaerythritol metal formate precipitation diluent preferably is methanol. It is highly preferred to use methanol both in step(3) and in the step(1) resin bed regeneration procedure. As illustrated in FIG. 1, methanolic streams containing organic byproduct can be transferred through lines 73 and 93, respectively, to the same distillation column 72, to yield methanol for recycle (line 77) and a residual organic byproduct stream for incineration (line 78).

With further reference to the invention process, the metal formate-enriched aqueous stream recovered in step(5) is recycled to step(1) to increase the efficiency of the overall process, and concomitantly to eliminate a prospective waste disposal problem.

In accordance with the practice of the present invention process, under optimal conditions at least about 85 percent of the metal formate and at least about 90 percent of the pentaerythritol contained in the original aqueous waste stream are recovered as useful products of the process. Further, the residual byproduct waste streams produced in the process have fuel value and are readily disposed of by incineration.

BRIEF DESCRIPTION OF THE DRAWINGS

Process embodiments of the present invention are illustrated in the accompanying drawings which are described as follows.

DESCRIPTION OF THE PREFERRED EMBODIMENTS

Figure 1:
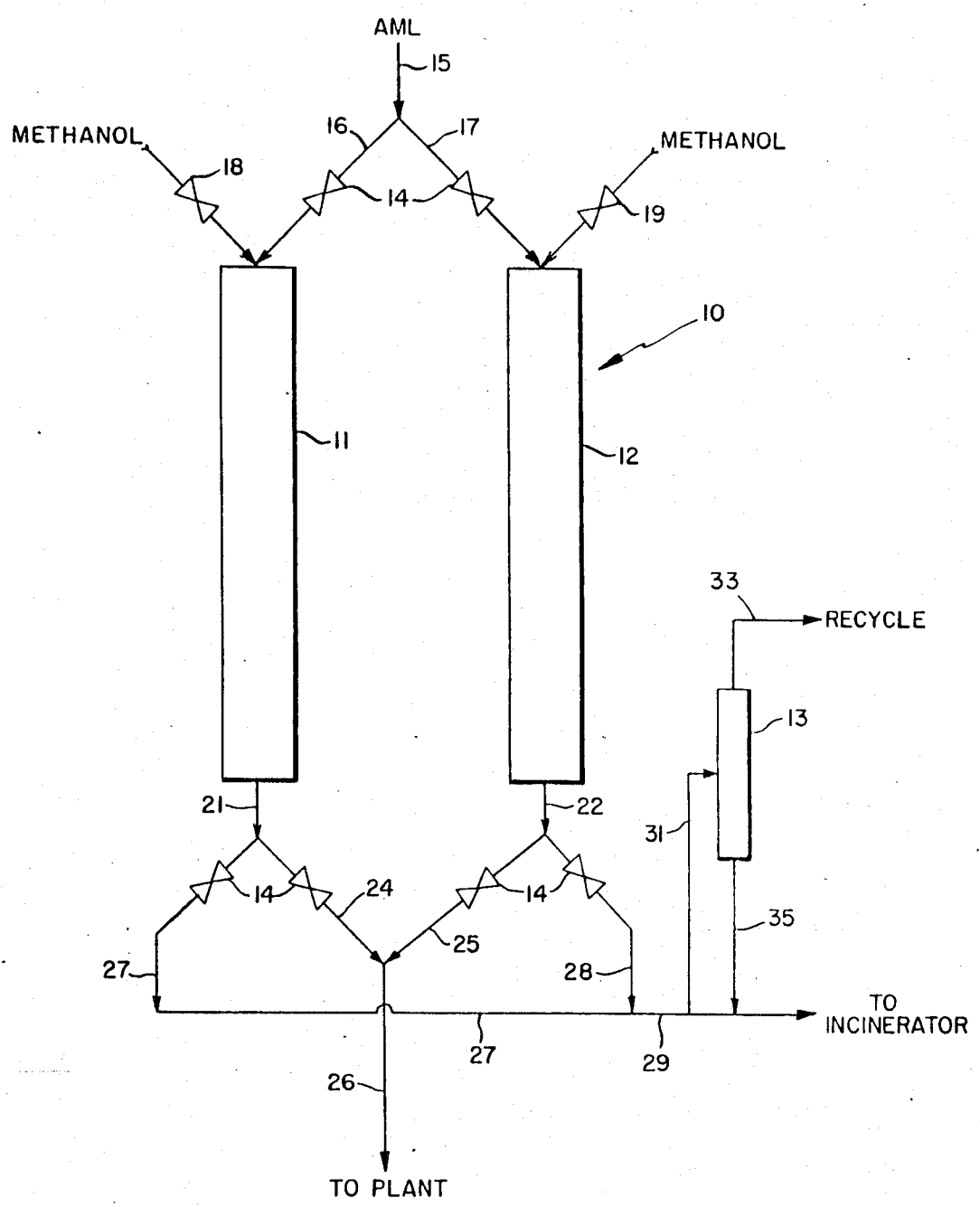
FIG. 1 is a flow sheet for step(1) of the invention process, and resin bed regeneration with an eluant.

The invention process is further delineated by the following Examples. Example I illustrates a process conducted according to prior art teachings, and Examples II-III illustrate the invention and its improvements. FIG. 1 relates to Example II, and FIG. 2 relates to Example III.

EXAMPLE I

A sodium dithionite manufacturing plant recovers sodium formate by evaporative crystallization of a pentaerythritol (PE) process waste stream composed of sodium formate (28-32%), organics (8-14%) and water (56-62%). Sodium formate recoveries of 60-75% are obtained by this method, and a process waste stream of significant volume is generated. This process waste stream contains sodium formate (36-44%), PE (14-18%) and other organic impurities (18-22%), with the balance as water. Incineration of the waste stream is complicated by flame instability and sodium carbonate buildup from combustion of sodium formate.

EXAMPLE II

The basic process described herein enables the sodium formate and pentaerythritol values to be separated from the organic impurities and utilized in the production process of another plant while producing a waste stream that is rich in combustible organic materials.

The process involves flowing the pentaerythritol proceess waste stream through a macroreticular resin bed (such as Rohm and Haas Amberlite XAD-7) which selectively adsorbs organic impurities while allowing PE and sodium formate to pass. Once the capacity of the bed has been reached (3 to 4 bed volumes), the column can be regenerated readily by elution of the organic impurities with methanol. The PE and sodium formate mixture can be sent to another plant process for manufacturing or recovery. The methanol from the regeneration step is totally or partially recovered by distillation, and the residual organic byproduct stream therefrom is incinerated. This organic byproduct stream has excellent incineration characteristics.

The waste treatment plant 10 of FIG. 1 comprises a pair of macroreticular resin beds 11-12, a stripper distillation column 13, and a plurality of flow-control valves 14 which are suitably positioned on flow lines connected thereto. Beds 11-12 are used and regenerated alternately. An AML waste stream, from a pentaerythritol production plant that utilizes the reaction of formaldehyde with acetaldehyde in the presence of sodium hydroxide catalyst, enters plant 10 through line 15 and respectively flows to the top of bed 11 or 12 through line 16 or 17, depending upon which bed is in use, and flows from the bottom thereof through line 24 or 25 and through line 26 to another plant, wherein sodium formate and pentaerythritol are recovered. An Amberlite XAD-7 type of acrylic ester resin is preferably utilized in beds 11-12, but other macroreticular resins can be substituted if they can achieve equivalent results.

Methanol, for regenerating the resin in beds 11-12, enters plant 10 and beds 11-12 through lines 18-19 and leaves the bottoms thereof through lines 27-28. The entire regeneration stream can be fed to the incinerator through line 29 or can be fed to stripper column 13 through line 31. The residual bottoms fraction, consisting almost entirely of organic byproducts, from stripper column 13 joins line 29 through line 35, and the overhead, consisting of methanol, leaves column 13 through line 33 which is connected to lines 18-19. The residual bottoms fraction entering the incinerator through line 29 burns without difficulty. Beds 11-12 are 5000-gallon beds which are operated at 8 hours to capacity.

The flow rates, in pounds per hour, are as follows in the designated lines which are listed at the left side of Table I, in which bed 11 is considered to be in use for removing organics and bed 12 is considered to be in use for regeneration. The corresponding volumetric flow rate for methanol is 1250 gallons per hour.

TABLE I

| Stream | Total lb/hr | H₂O lb/hr | NaCO₂H lb/hr | PE lb/hr | Organics lb/hr | MeOH lb/hr |
|---|---|---|---|---|---|---|
| 16 | 24,000 | 12,744 | 6,288 | 1,272 | 3,696 | — |
| 24 | 21,315 | 12,746 | 6,288 | 1,279 | 1,002 | — |
| 19 | 8,250 | — | — | — | — | 8,250 |
| 28 | 10,944 | — | — | — | 2,694 | 8,250 |
| 33 | 7,838 | — | — | — | — | 7,838 |
| 35 | 3,107 | — | — | — | 2,694 | 413 |

The percentages of the components in the pentaerythritol process waste stream and purified waste streams in lines 15-16 and 21, 24 and 26, respectively, are as follows on a weight percentage basis:

TAble II

| Stream | Total % | H₂O % | NaCO₂H % | PE % | Organics % | MeOH % |
|---|---|---|---|---|---|---|
| 15,16 | 100.0 | 53.1 | 26.2 | 5.3 | 15.4 | 0.0 |
| 21,24,26 | 100.0 | 59.8 | 29.5 | 6.0 | 4.7 | 0.0 | pentaerythritol recovery and facilitate centrate handling, while all of the pentaerythritol waste stream feed is used to wash the cake of mixed sodium formate and pentaerythritol crystals in order to extract the sodium formate thoroughly and produce pure pentaerythritol.

Figure 2:
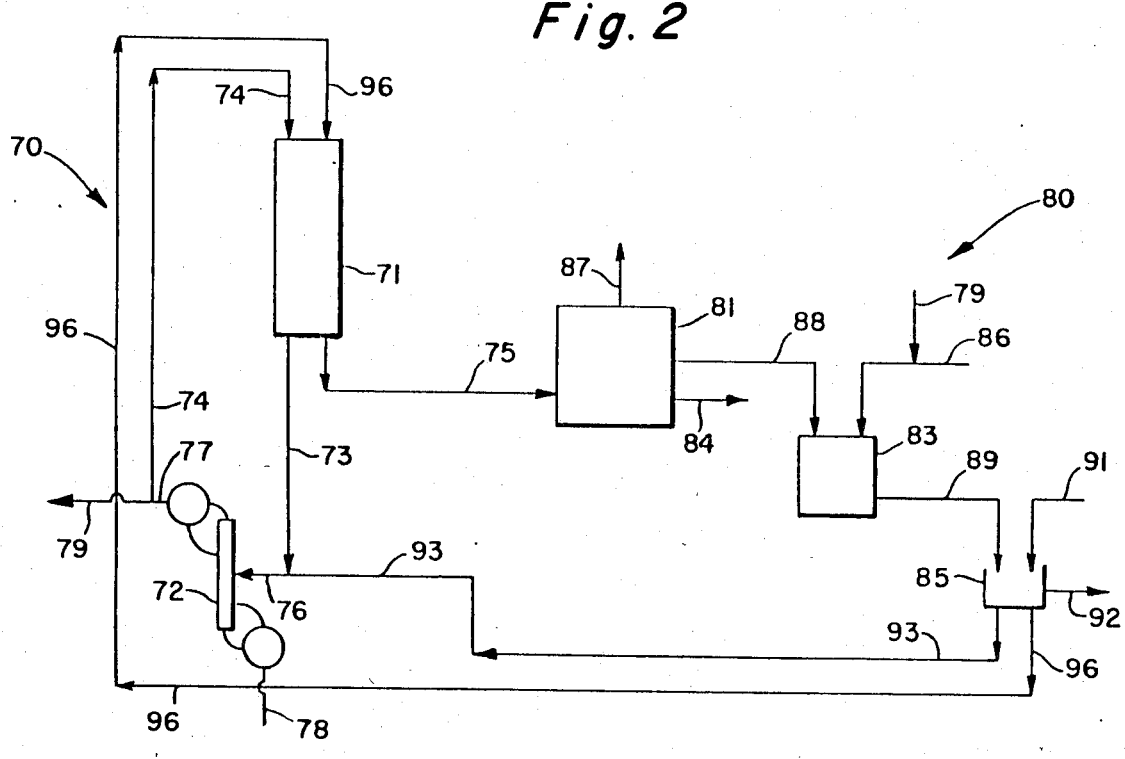
FIG. 2 is a flow sheet for a metal formate-enriched aqueous waste stream feed embodiment.

The organics removal operation 70 is combined with the crystallization operation 80, as seen in FIG. 2 Macroreticular resin beds 71 are fed with a sodium formate-enriched pentaerythritol waste stream in line 96 and are regenerated with methanol in line 74. The partially purified pentaerythritol waste stream flows from the bottom of bed 71 and then through line 75 to crystallization operation 80. Organics-rich methanol flows from the bottom of bed 71 which is being regenerated and then through line 73 and combines with second centrate in line 93 to become feed for stripper column 72 that enters through line 76. Bottoms from column 72 flows through line 78 to the incinerator. An overhead stream leaves column 72 through line 77 and in part passes through line 74 as feed for regenerating bed 71 and in part is recycled to the process through line 79.

The partially purified pentaerythritol waste stream is evaporated in apparatus 81, forming crystals of sodium formate which are removed through line 84. Condensate is removed through line 87. The mother liquor or first centrate flows through line 88 to methanol cooling tank 83 wherein it is mixed with make-up methanol in line 86 and recycled methanol in line 79 at a weight ratio of 2:1 centrate:methanol and cooled to 40° C., forming a slurry which moves through line 89 to centrifuge 85. The organics-rich second centrate flows through line 93 to join organics-rich methanol in line 73. The cake is washed with all of the feed pentaerythritol waste stream in line 91 to leach out all of the sodium formate. The remaining crystals of highly purified pentaerythritol are removed through line 92. The sodium formate-rich pentaerythritol waste stream flows through line 96 to become feed for bed 71.

The flow rates, in pounds per hour, are listed in Table III for the total flows and for their components: water, sodium formate, pentaerythritol, organics, and methanol.

TABLE III

| Stream | Description | Total lb/hr | H₂O lb/hr | NACO₂H lb/hr | PE lb/hr | Organics lb/hr | MeOH lb/hr |
|---|---|---|---|---|---|---|---|
| 75 | Resin Effluent | 22,532 | 12,914 | 8,115 | 1,087 | 416 | — |
| 87 | Overhead Condensate | 11,746 | 11,746 | — | — | — | — |
| 84 | Formate Product | 5,997 | — | 5,997 | — | — | — |
| 88 | Centrate I | 4,789 | 1,168 | 2,118 | 1,087 | 416 | — |
| 86 | Make-up MeOH | 97 | — | — | — | — | 97 |
| 79 | MeOH | 2,087 | — | — | — | — | 2,087 |
| 89 | Mixture | 6,973 | 1,168 | 2,118 | 1,087 | 416 | 2,184 |
| 91 | AML | 22,064 | 12,914 | 6,677 | 1,087 | 1,386 | — |
| 92 | PE Product | 1,066 | — | — | 1,066 | — | — |
| 93 | Centrate II | 4,469 | 1,168 | 680 | 21 | 416 | 2,184 |
| 96 | Enriched AML | 23,502 | 12,914 | 8,115 | 1,087 | 1,386 | — |
| 78 | To Incinerator | 3,352 | 1,168 | 680 | 21 | 1,386 | 97 |
| 73 | Resin Clean-up | 4,910 | — | — | — | 970 | 3,940 |
| 74 | MeOH | 3,940 | — | — | — | — | 3,940 |

EXAMPLE III

The sodium formate-enriched pentaerythritol waste stream embodiment in which the partially purified PE waste stream described in Example II is treated to produce a substantially pure sodium formate product and a highly purified pentaerythritol product, is illustrated in FIG. II. In this process methanol is used to enhance The sodium formate recovery is increased to approximately 90% from 75%; the PE recovery approaches 98%. The incinerator stream has a heating value of 5000 BTU/lb, and the sodium formate concentration is reduced to about 20% from 44%. The stream volume is reduced by approximately 30%.

The more pentaerythritol waste stream feed that is used for washing the cake of mixed sodium formate and pentaerythritol crystals, the purer is the resultant pentaerythritol product. In addition, the larger the proportion of the pentaerythritol waste stream feed that passes through the macroreticular resin bed, the purer are the crystalline products that are obtained from the evaporative and cooling crystallization processes. Therefore, the sodium formate-enriched waste stream feed process of Example III is most highly preferred.

Methanol is preferably used for regenerating the macroreticular resin beds because it is readily utilized in other parts of the process, such as in the stripper columns, but other waste-miscible alkanols can be employed, as well as other water-miscible solvents such as acetone, dimethylsulfoxide, tetrahydrofuran, dimethylformamide, and the like. Hot water and saturated steam can also be used for regeneration.

What is claimed is:

1. A process for recovering inorganic and organic values from an aqueous waste stream derived from pentaerythritol production in which formaldehyde is reacted with acetaldehyde in the presence of a metal hydroxide catalyst, wherein said aqueous stream contains metal formate, pentaerythritol and organic byproducts, said process comprising (1) passing the aqueous waste stream through a macroreticular acrylic ester resin bed to remove organic byproducts and provide a purified aqueous waste stream; (2) evaporatively. crystallizing the purified aqueous waste stream to form crystalline metal formate and a concentrated aqueous mother liquor; (3) separating and recovering the crystalline metal formate as a product from the concentrated aqueous mother liquor, and diluting the said mother liquor with water-miscible alkanol to form a precipitated pentaerythritol-metal formate crystalline mixture and an aqueous alkanolic mother liquor; (4) separating the pentaerythritol-metal formate crystalline mixture from the aqueous alkanolic mother liquor; and (5) contacting said crystalline mixture with a portion of the original aqueous waste stream to dissolve selectively the crystalline metal formate and form a metal formate-enriched aqueous waste stream, and yield undissolved crystalline pentaerythritol as a product.

2. A process in accordance with claim 1 wherein the metal hydroxide catalyst is sodium hydroxide, and the metal formate is sodium formate.

3. A process in accordance with claim 1 wherein the macroreticular acrylic ester resin in step(1) is further characterized by the following nominal properties:

| Solids, % | 28-33 |
| Porosity, ml pores/ml bead | 0.5-0.55 |
| Surface area, sq. m/gm dry basis | 440-460 |
| Average pore diameter, Å | 75-85 |
| True wet density, gm/ml | 1.0-1.1 |
| Skeletal density, gm/ml | 1.2-1.3 |
| Bulk density, gm/cc | 0.6-0.7 |

4. A process in accordance with claim 1 wherein the water-miscible alkanol in step(3) is methanol.

5. A process in accordance with claim 1 wherein the recovered aqueous alkanolic mother liquor in step(3) is subjected to distillation to yield alkanol for recycle and a residual organic byproduct stream.

6. A process in accordance with claim 1 wherein the metal formate-enriched aqueous waste stream recovered in step(5) is recycled to step(1) or step(2).

* * * * *